United States Patent [19]
Wick et al.

[11] Patent Number: 6,051,189
[45] Date of Patent: Apr. 18, 2000

[54] SYSTEM AND METHOD FOR DETECTION, IDENTIFICATION AND MONITORING OF SUBMICRON-SIZED PARTICLES

[75] Inventors: Charles H. Wick, Darlington, Md.; David M. Anderson, Cary, N.C.

[73] Assignee: The United States of America as represented by the Secretary of the Army, Washington, D.C.

[21] Appl. No.: 08/941,990

[22] Filed: Oct. 1, 1997

[51] Int. Cl.⁷ .................................................... G01N 27/00
[52] U.S. Cl. .................... 422/82.01; 73/28.01; 73/28.04; 73/31.02; 422/70; 422/72; 422/81; 422/83; 422/101; 435/239; 436/36; 436/86; 436/89; 436/94; 436/161; 436/177; 436/181; 530/334
[58] Field of Search ................................ 73/28.01, 28.04, 73/31.02; 422/83, 70, 72, 81, 101, 82.01; 436/94, 86, 89, 36, 161, 177, 181; 435/239, 5, 6; 530/334

[56] References Cited

U.S. PATENT DOCUMENTS 3,759,617  9/1973  Barringer .
4,217,418  8/1980  McAleer et al. .
5,076,097  12/1991  Zarrin et al. .
5,247,842  9/1993  Kaufman et al. .
5,606,112  2/1997  Flagan et al. .
5,645,715  7/1997  Coombs .

OTHER PUBLICATIONS

Sheehan et al., Biochem. J. (1996) v.315, pp. 1055–1060.
Webster's Ninth New Collegiate Dictionary, Merriam Webster Inc. (1987) pp. 350 and 1279.

*Primary Examiner*—Jan Ludlow
*Attorney, Agent, or Firm*—William W. Randolph; Ulysses John Biffoni

[57] ABSTRACT

A system and method for detection, identification, and monitoring of submicron sized particles, the method including the steps of collecting a sample, extracting existing submicron particles from the collected sample based on density, purifying the extracted submicron particles by concentrating the extracted submicron particles based on size, and, detecting and identifying the purified extracted submicron particles based on size and density thereby determining submicron particles present in the collected sample. The submicron particles detected and identified include viruses and virus-like agents such as prions. Thus, virus and virus-like agents can be detected and identified based only on their physical properties without the use of biochemical reagents or assays. A system for carrying out the method of detection and identification of these particles is also disclosed.

4 Claims, 7 Drawing Sheets

ALL VIRUSES PATHOGENIC TO MAN PLOTTED BY SEDIMENTATION COEFFICIENT AND DENSITY

KEY:

- A. Microsomal Background
- B. Adenoviridae
- C. Arenaviridae
- D. Astroviridae
- E. Caliciviridae
- F. Coronaviridae
- G. Filoviridae
- H. Hepadnaviridae
- I. Herpesviridae
- J. Orthomyxviridae
- K. Papovaviridae
- L. Paramyxviridae
- M. Retroviridae
- N. Flaviviridae
- O. Parvoviridae
- P. Picornaviridae
- Q. Poxviridae
- R. Togaviridae
- S. Bunyaviridae
- T. Reoviridae
- U. Rhabdoviridae

| Legend | Virus Family | Range of Density, size | Preferred range of density, size |
|---|---|---|---|
| B | Adenoviridae | 1.30-1.39, 67-115 | 1.32-1.35, 80-110 |
| C | Arenaviridae | 1.18-1.25, 45-300 [1.27-1.36, 40-290] | 1.19-1.24, 50-150 |
| D | Astroviridae | 1.35-1.44, 26-32 | 1.35-1.40, 27-31 |
| E | Caliciviridae | 1.32-1.45, 28-40 | 1.33-1.40, 29-39 |
| F | Coronaviridae | 1.18-1.26, 80-170 [1.25-1.33, 100-160] | 1.23-1.25, 120-160 |
| G | Filoviridae | 1.30-1.40, 75-400 [1.32-1.39, 70-390] | 1.31-1.34, 80-230 |
| H | Hepadnaviridae | 1.23-1.30, 30-45 [1.33-1.38, 24-40] | 1.24-1.26, 34-42 |
| I | Herpesviridae | 1.19-1.33, 90-200 [1.25-1.35, 90-180] | 1.20-1.30, 100-180 |
| J | Orthomyxoviridae | 1.18-1.26, 75-125 [1.25-1.34, 65-110] | 1.19-1.26, 80-120 |
| K | Papovaviridae | 1.19-1.36, 35-57 | 1.31-1.34, 40-55 and 1.19-1.24, 37-42 |
| L | Paramyxoviridae | 1.18-1.27, 100-300 [1.25-1.33, 90-280] | 1.18-1.26, 130-200 |
| M | Retroviridae | 1.15-1.24, 70-120 [1.24-1.29, 70-95] | 1.17-1.23, 80-100 |
| N | Flaviviridae | 1.14-1.28, 30-65 [1.25-1.32, 30-55] | 1.20-1.26, 40-60 |
| O | Parvoviridae | 1.38-1.45, 17-27 | 1.38-1.42, 18-26 |
| P | Picornaviridae | 1.30-1.46, 20-30 | 1.31-1.44, 22-30 |
| Q | Poxviridae | 1.28-1.35, 140-370 [1.29-1.38, 130-360] | 1.29-1.33, 150-350 |
| R | Togaviridae | 1.17-1.27, 60-85 [1.24-1.33, 58-70] | 1.19-1.25, 65-80 |
| S | Bunyaviridae | 1.15-1.24, 80-130 [1.25-1.30, 70-110] | 1.19-1.22, 80-120 |
| T | Reoviridae | 1.35-1.43, 55-85 | 1.36-1.39, 65-85 |
| U | Rhabdoviridae | 1.17-1.23, 45-300 [1.20-1.27, 40-290] | 1.18-1.21, 50-220 |

FIG. 7

SYSTEM AND METHOD FOR DETECTION, IDENTIFICATION AND MONITORING OF SUBMICRON-SIZED PARTICLES

GOVERNMENT INTEREST

The invention described herein may be manufactured, licensed, and used by or for the United States Government.

BACKGROUND OF THE INVENTION

1. Field of the Invention

The present invention relates to the detection, identification and monitoring of submicron size particles. More particularly, the invention pertains to a device and method for automated detection, identification, and monitoring which samples submicron size particles. Preferably, the present invention provides for the sampling, detection and identification of viruses and virus-like agents (such as, for example, prions, viral subunits, viral cores of delipidated viruses, etc.) in bioaerosols and fluids, especially biological fluids.

2. Brief Description of the Related Art

Detection and identification of viruses without limiting the detection and identification to a particular family, genus and species is extremely difficult. Searching for viruses pathogenic to humans in a single environment is also extremely difficult Additionally, sampling viruses and virus-like agents in air, as well as other fluids, increases the complexity of the detection and monitoring.

The difficulty of detecting and monitoring a wide range of viruses also varies by environment, but perhaps the most troublesome environment involves combat conditions. In particular, the problem of detecting and monitoring viruses in a potential biological warfare (BW) threat environment is extremely demanding. Notwithstanding the variation in virulence from virus to virus, a generally accepted figure is that ingestion of $10^4$ virions constitutes a significant threat to a soldier who breathes on the order of 1,000 liters (1 m$^3$) of air per hour. Instruments with sensitivities which enable detection of remote releases of biological agents in a field environment thereby providing early warning capabilities, allowing calculations for troop movements and wind patterns, have been previously lacking.

Additionally, it has been previously difficult to maintain a broad-spectrum system for the detection of viruses which is free from false negatives because of natural or artificial mutations. The high mutation rates of known viruses, as well as the emergence of new viruses, such as the Ebola virus, must be addressed by any detection method. The potential for deliberate artificial mutations of viruses also exists. Furthermore, there are virus-like infectious agents, such as prions, which are suspected in causing scrapie, "mad-cow disease" and Creutzfeldt-Jakob disease. These prions possess no DNA or RNA, and can withstand 8 MRads of ionizing radiation before losing infectiousness. Other virus-like infectious agents, such as satellites, possess no proteins. However, detection of all of these agents must be possible for a device or method to be generally effective in the detection and monitoring of viruses and similar agents (such as, for example, virus fragments, prion, satellites, etc.) which are pathogenic to humans.

Detection and monitoring of viruses must also be free from false positives associated with background. Background includes biological debris which obscures the detection of the viruses by registering as a virus with the detection methods used in analyzing the samples collected. Analysis of viruses requires a very high degree of purification of those viruses to overcome background loading in order to avoid false positives. For example, a BW virus may be buried within loadings of other microorganisms which form biological debris having loading on a magnitude of $10^{10}$ larger than the threshold loading for the targeted virus itself.

Although methods that culture viruses can often be used to increase the virus over background, culture methods are too slow for efficient viral BW detection; furthermore, some important viruses cannot be cultured by known methods, and in any case cell culture is a highly variable and inconsistent method.

Viruses may also be extracted from an environment and concentrated to an amount that is required for detection and monitoring, without requiring any culturing. Quite generally, in the detection of small amounts of viruses in environmental or biological liquids, it is necessary to both enrich the concentration of viruses many orders of magnitude (i.e., greatly reduce the volume of liquid solubilizing the viruses) and accomplish exquisite removal of non-viral impurities; in the presence of non-viral impurities, even the most sensitive detection methods generally require virus concentrations on the order of 10 femtomoles/microliter or more in the sampled liquid in order to reliably detect the viruses.

Sampling for airborne viruses is generally accomplished by collecting airborne particles into liquid, using a process such as air scrubbing, or eluting from filter paper collectors into liquid. Since collection and subsequent separation and detection methods are strongly affected by the adsorption of viruses to solids in aerosols and by solids-association in water, this poses stringent requirements on the design of the sampling of air for viruses.

In contrast, when sampling liquids for viruses, in many cases no special equipment or processes may be necessary in order to collect a sample; for example, in sampling blood for viruses, only a standard clinical hypodermic needle may be needed, and similarly for other body liquids. For sampling of bodies of water or other conveniently accessible liquids, sample collection may not be an issue at all, and in such cases the term "collector" is often applied to what is, in reality, a virus extraction step (such as collection on a filter).

Currently, there is no simple and rapid method or device for detection of viruses which are pathogenic to humans in a BW environment. Rapid detection translates into protection for soldiers, more reliable and simplified strategic planning, and validation of other BW countermeasures. Previously known detection methods using biochemical reagents are impractical in the field, even for trained virologists. Additionally, reagent-intensive approaches, such as multiplex PCR, low-strigency nucleic acid hyridization, and polyclonal antibodies, increase the incidence of false positives several hundred-fold, whether under highly idealized laboratory conditions or in the field. Additionally, the hypervariability, or rapid mutation, of viruses and emergence of new, uncatalogued viruses precludes methods based on biochemical assays, such as PCR, immunoassay, and the like, from achieving broad-spectrum detection— detection of all viruses regardless of identity, known or unknown, sequenced or unsequenced.

There is a need for a highly reliable automated system.

In view of the foregoing, improvements in the detection and monitoring of submicron particles have been desired. In addition to increasingly rapid time response for the detection and monitoring of a universal sampling of viruses, an automated system is needed. Computer control of instruments and data collection/interpretation provides advantages of increased operator safety, simultaneous multiple location detection, decreased operator training and a greater consistency of results.

SUMMARY OF THE INVENTION

In view of the foregoing, it is therefore an object of the present invention to provide a system for universal monitoring and sampling for viruses.

Another object of the present invention is to provide a method and device for rapid detection and identification of viruses which is based on the physical characteristics of viruses and therefore does not require the use of biochemical reagents or assays.

It is a further object of the present invention to provide an automated system for the detection of viruses and virus-like agents.

Additionally, it is an object of the present invention to detect known and unknown or mutated viruses which are pathogenic to humans.

These and other objects are achieved by the present invention which includes a method for detection of submicron sized particles comprising the steps of:

(a) collecting a sample (this is generally trivial in the case of waterborne or bloodborne particles, but nontrivial in the case of airborne particles);

(b) extracting existing submicron particles from said collected sample based on density, (c) purifying said extracted submicron particles by concentrating said extracted submicron particles based on size; and (d) detecting said submicron particles based on the density and size of said extracted, purified submicron particles.

In another aspect of the invention the method further comprises counting the extracted and purified submicron particles and identifying said submicron particles.

In another aspect of the present invention, there is provided a device for detection of submicron particles comprising a collector for collection of a sample, an extractor for extracting submicron particles from said collected sample, a purifier which concentrates said submicron particles, and, a detector that detects and identifies said purified and concentrated submicron particles.

The method and system of the present invention are extremely valuable in the field of virus detection. Other and further advantages of the present invention are set forth in the description and appended claims.

DETAILED DESCRIPTION OF THE PREFERRED EMBODIMENTS

The present invention is a method and device for the detection and monitoring of submicron particles. The method and device allow for collection, extraction, purification and detection of viruses which are pathogenic to humans. The method and device permit an automated system for the rapid detection and monitoring of these viruses.

Figure 6:
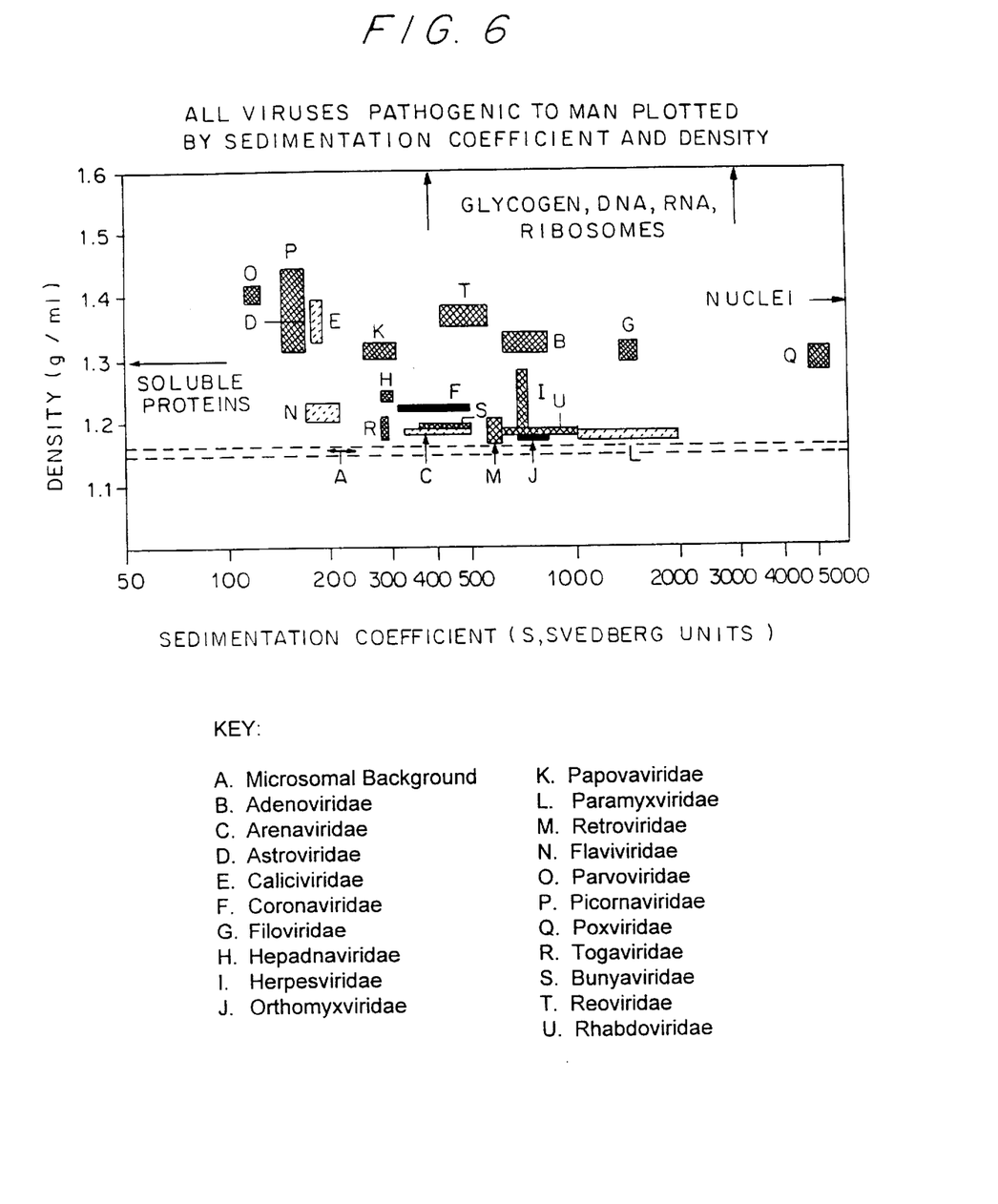
FIG. 6 is a plot of the virus window showing the densities and sedimentation coefficients for viruses pathogenic to man.
Figure 7:
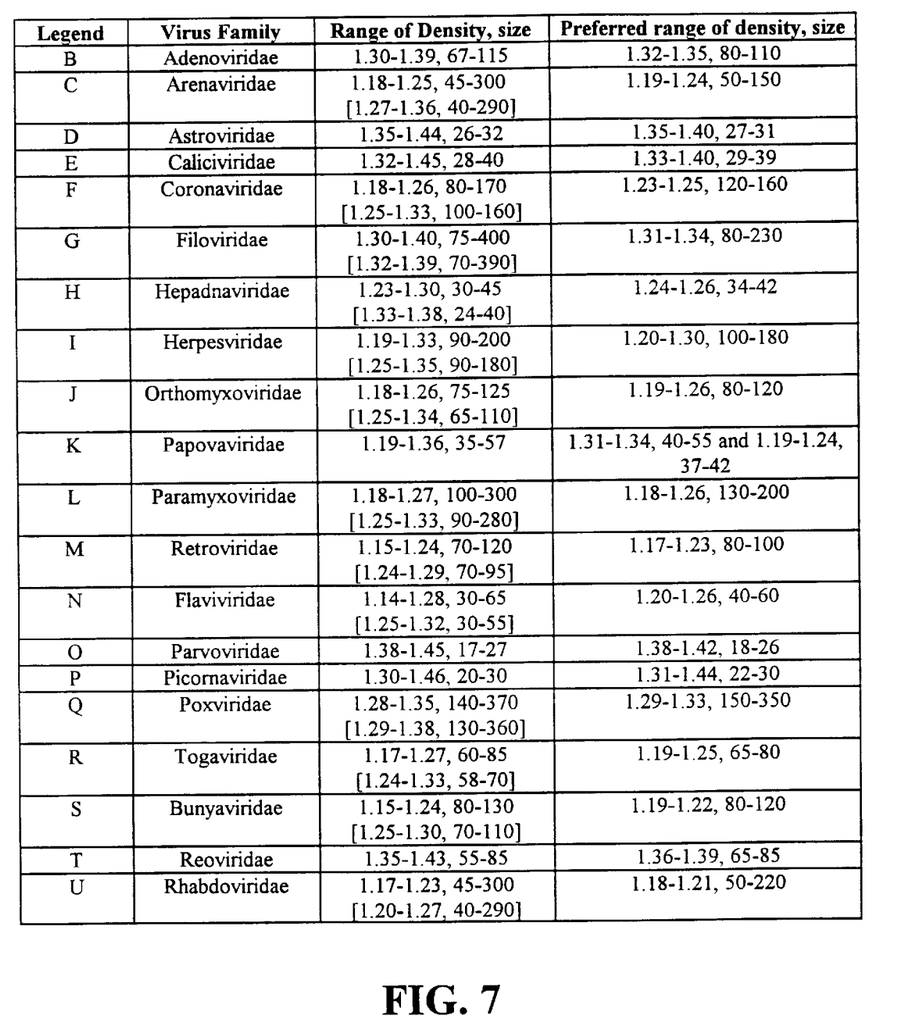
FIG. 7 provides a table giving the densities (g/ml) and size (nm) for known viral families containing species pathogenic to man.

The invention achieves synergistic use of centrifugation and ultrafiltration virus-purification methods. Centrifugation separates viruses from non-viral impurities, by using large centrifugal forces to break virus particles away from solids, cells and cell substructures, but without a high concentrating effect. Ultrafiltration performs a purification and a concentration of many orders of magnitude on the viruses after the viruses are separated from extraneous material in the centrifugation step. Furthermore, together these methods select viruses from the background based on both density with isopycnic banding centrifugation and size with ultrafiltration. Neither of these properties alone is sufficient to distinguish viruses from extraneous particles. In particular, proteins have densities which overlap with those of viruses, and microsomes, glycogen and other cell structures and macromolecules have sizes which overlap with those of viruses, but none of these overlap with viruses in both density and size. By combining these properties, a "virus window" can be constructed. A diagram of the virus window for all viruses pathogenic to man is provided as FIG. 6. The data disclosed in the virus window can be used to identify viruses in collected samples.

A feature which is incorporated into the present invention is the fact that density-gradient centrifugation (isopycnic banding) separation allows a single stage not only to separate viruses from non-viral material based on density, but also effects a substantial degree of protein removal, regardless of density. This allows removal of proteins which are ubiquitous in sampled fluids and have densities that overlap with those of viruses. A substantial removal of proteins in this stage complements the subsequent removal in the ultrafiltration and DMA stages.

Figure 1:
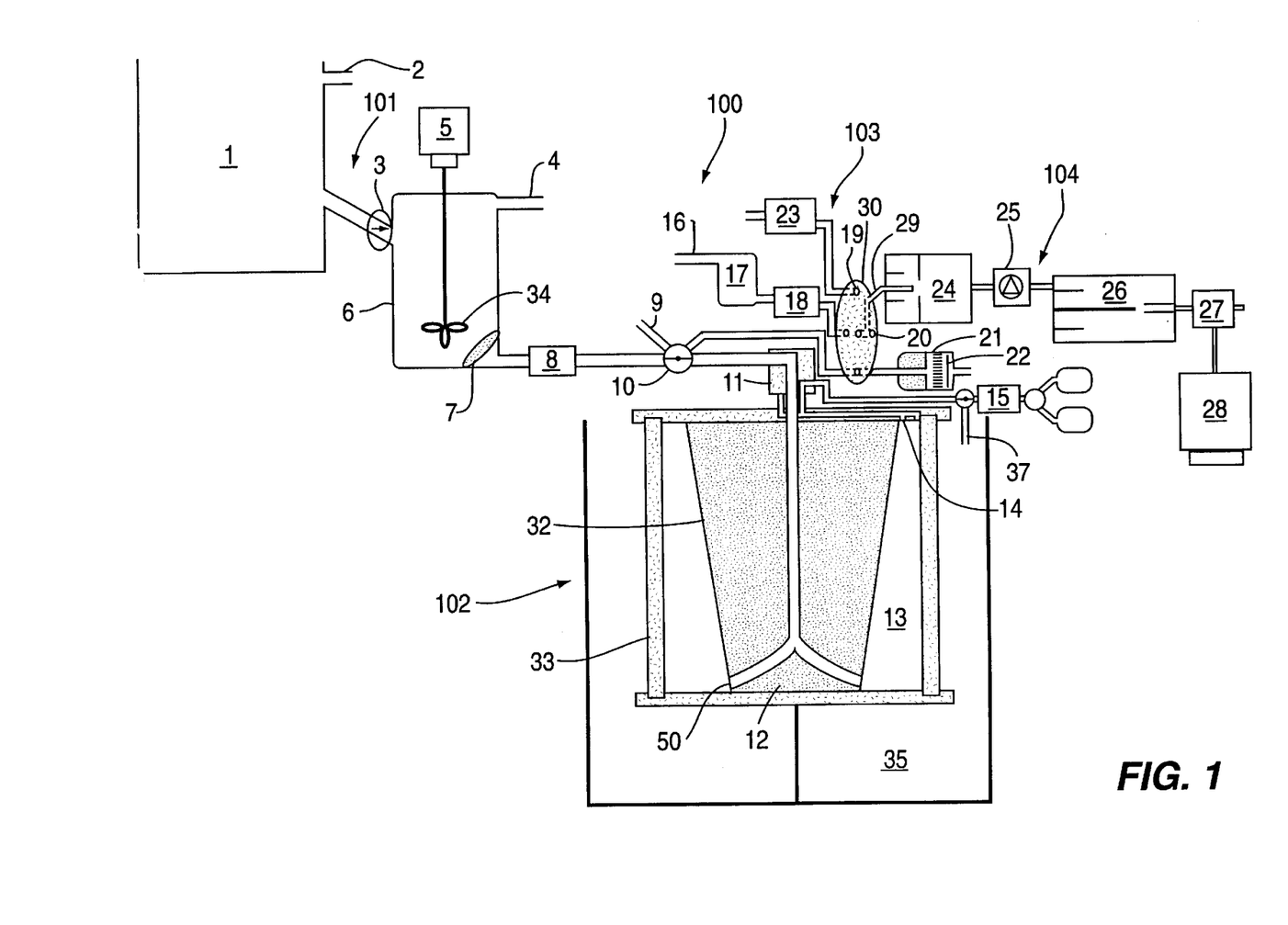
FIG. 1 is a schematic illustration of the integrated virus detection system of the present invention.

Referring now to FIG. 1, an integrated virus detection system (IVDS) 100 of the present invention is shown. The IVDS includes a collection stage 101, an extraction stage 102, a purification/concentration stage 103, and a detection stage 104. These four stages are herein further described.

In the collection stage 101, a collector 1 is used for aerosol or gaseous fluid sampling. In aerosol sampling, the collector 1 samples airborne particles having sizes which optimally carry viruses, preferably a size of 2–10 microns, and at collection rates of 1,000 liters/min of air. Collection of the submicron size virus particles in the collector 1 is facilitated by the fact that airborne viruses generally travel in or on aerosol particles which measure larger than a micron. In exceptional cases where the virus is not rafting on a super-micron fomite, the danger of transmission by inhalation is generally reduced because of the distribution of submicron particles in the atmosphere and the difficulty in capture by the lungs. The collector 1 has a water inlet 2 which is connected to a water source, such as tap water or other water purification system. The collector 1 scrubs the collected particles with the incoming water from the water inlet 2. Examples of the collector 1 are the U.S. Army's XM2 or the SPINCON collector made by Midwest Research Institute.

In many applications other than aerosol sampling, specimens possibly containing, for example, viruses are obtained without need for what would be considered a formal "collection stage", in particular when the specimen is already in liquid form. These include, for example, blood samples, obtained by ordinary means familiar in clinical settings, as well as other body fluids such as mucus, semen, feces, lymph, saliva, etc. Also in this category are situations involving sampling of bodies of water such as municipal water supplies, rivers and lakes, beverages, and high-purity water for microelectronics manufacture. The situation in general can be summarized by noting that, within the context of the present invention, as well as quite generally, detection of viruses or other particles in aerosols involves an additional step and additional equipment that, in the case of liquid sampling, is not required but rather other collecting means will generally be associated with obtaining the samples.

The collector 1 further has tubing 3 which connects the collector 1 to a holding tank 6 having a blender or homogenizer 5. The collector 1 has an aqueous stream output on the order of 1–10 ml/minute containing the scrubbed particles which is pumped through the tubing 3, which is preferably TEFLON or polysiloxane-coated to reduce adsorptive losses. The tubing 3 goes preferably to a one liter holding tank 6. Alternatively, the tubing 3 goes directly to the extraction stage 102.

In the holding tank 6, solids in the aqueous stream are broken up by using the homogenizer 5, or alternatively, by forcing the aqueous stream through an orifice. The homogenizer 5 has a bladed section 34. Surfactant or amphiphile is added at the inlet 4, which preferably is mixed with water prior to entry into the holding tank 6. The surfactant or amphiphile breaks down the structures in the aqueous stream. Preferably, the amphiphile has a low boiling point, which allows easy removal of the amphiphile in a later stage. Most preferred, the amphiphile is diethylene glycol monohexyl ether. Base is also preferably added to increase the pH of the homogenized liquid which tends to decrease aggregation. Examples of the homogenizer 5 are the Lightnin Closed Tank Model general purpose stirrer model G2S05R, available from Lightnin, a unit of General Signal of Avon, N.Y., catalog no. 869435, or the PC-controllable stirring motor, RE162 analog, ID no. 8000700 and rotor-stator S 50 N-W 65 SK, ID no. 8005100 from IKA Works, Inc. of Cincinnati, Ohio, which serves as part 34.

In leaving the holding tank 6, the aqueous stream passes a screen filter 7 which regulates the output of the holding tank 6. The screen filter 7 is preferably 10 micron mesh and made of stainless steel or other corrosion-free material. A pump 8, which is designed for pumping liquids through the tank 6, draws the aqueous stream from the holding tank 6 and through the screen filter 7.

Beyond the pump 8, a three-position PC-controlled switch 10 is used to allow the discharge from pump 8 to flow into a centrifuge rotor 12 in a first position. To understand the function of the second and third positions of this switch, it is necessary to realize that after centrifugation, the gradient imprisoned in the rotor can be divided into two parts: the useful part which contains that range (or in some cases, those ranges) of densities in which the particles to be detected are expected to lie, and the remainder which will generally be discarded and not sent on to the next stage. Thus, for example, in the detection of viruses pathogenic to humans, this useful part could be that part of the gradient corresponding to densities of 1.175–1.46 g/ml, as discussed elsewhere herein; alternatively, a subset of this range could constitute the useful range if only certain viruses are being analyzed for.

Thus, the second position of switch 10 allows the useful part of the gradient to flow on to part 30 (in particular, to the first position of part 30, as discussed below), and the third position of the switch allows the discarded portion of the gradient from the rotor 12 to flow out through a port 9; if desired, port 9 can incorporate means to recycle density gradient material, if desired. In the first position, as the screen-filtered sample from the pump 8 travels past the switch 10, it enters into the extraction stage 102.

In the extraction stage 102, the aqueous stream enters a liquid-cooled coaxial seal 11. After passing the coaxial seal 11, the aqueous stream enters at the upper shaft of the rotor 12. The rotor 12 is a zonal ultracentrifuge rotor, such as a Beckman's CF-32 rotor or Z-60 rotor, which is inserted into and spun by a centrifuge 35, such as a Beckman Optima XL-100K Preparative Ultracentrifuge. For large sample volumes with small quantities of viruses, for example monitoring of bodies of water, such as drinking water sources, the present invention preferably uses continuous-flow density gradient ultracentrifugation, using for example the Beckman's CF-32 rotor. For other applications, ordinary zonal centrifugation is preferred with rotor 12 being a Beckman's Z-60 rotor. In a special seal and bearing assembly, fluid inlet and outlet streams access an annular space 13 between a core 32 and rotor wall 33 through the coaxial seal assembly 11 and via port 50. Density gradient solutions, sample liquid, and the displacement fluid are sequentially pumped into the annular space 13. Density gradient solutions are loaded from port 15 through inlet 14. From pump 8, sample liquid is added. A density gradient solution is any liquid which permit the separation of viruses, such as a sucrose or, preferably, cesium chloride solution.

In continuous flow operation, the virus-containing liquid stream is pumped in from the collection stage 101 and flows continuously over the density gradient in the rotor 12, and viruses sediment out of the stream, banding into the density gradient according to buoyant density. This pumping of sample into and out of the rotor 12 can be performed with the centrifuge spinning at high speed. The continuous stream allows a large volume of fluid to flow through the annular space 13, which permits virus material to be captured in the gradient, even with small concentrations of viruses in the fluid. In ordinary zonal operation (not continuous-flow), the sample does not flow continuously into the rotor for long periods of loading, but rather the entire sample volume, which must be less than the annular volume in the rotor, is loaded and enclosed in the rotor 12. The rotor volume is then closed off before acceleration to high speed. In either case, this is called the loading phase of the isopycnic banding separation. After loading and centrifuging to achieve banding, the virus-containing bands are recovered by displacing the bands sequentially, with lowest density bands exiting first and highest density last. As the density of each virus uniquely determines the position of that virus or particle in the exiting stream, the timing of the detection of specific virus particles provides particle density information.

A fresh gradient is loaded into the rotor 12 by pumping a low density fluid, containing no cesium chloride, into the rotor 12. As illustrated schematically by the presence of two fluid tanks and a mixing valve in part 15 of FIG. 1, a high density fluid, typically containing about 60% cesium chloride is mixed with the low density fluid at a variable high:low ratio, which via PC control increases with time until the loading is complete. The fluids pass through the fluid entry ports 14 at the top of the annular space 13. Concurrently, the rotor 12 is spinning at a low speed of about 4,000 rpm, with the speed being controlled by the timer control system in tandem with the fluid entry and displacement.

After the fresh gradient is loaded, the control system actuates valves which flow fluid through the rotor 12 in the opposite direction, pumping sample from the holding tank 6, through switch 10 (in the first position), through the bottom entry port 50, and upward through the annular space 13, entering at the bottom end and displacing fluid out at the top of the rotor 12 through 14 and out discharge port 37. After establishing flow reversal, the control system initiates and regulates the centifuge to a preferred rotational speed of about 60,000 rpm for a B-series rotor. In extremely dry environments, water exiting the centrifuge may be recycled back into the system by pumping it back into the collector 1 where it can be used for air scrubbing. At a rotational rate of 60,000 rpm and flow rate as high as 6 liters/hr, over 90% of all virus enters the gradient from the sample fluid stream, where it remains imprisoned. After on the order of 10–30 minutes of operation, which allows as much as 3 liters of sample fluid to pass through the rotor 12, the inflow and effluent flow are shut off, and the high-speed rotation continues for an additional 30 minutes to band the viruses. The viruses become banded in the gradient The centrifuge controls are actuated by a timer-regulated control system, which is preferably a standard PC-computer interface.

In operation, sample liquid is introduced into the density gradient within the centrifuge rotor at the low-density end of the gradient, and each particle or molecule penetrates into the gradient at a rate that increases with the mass of the particle, and with the density. In the case of a protein molecule, the mass is much smaller than that of a virus by at least an order of magnitude, and the density is about the same as that of a relatively low-density virus. Accordingly, the rate of banding for proteins is much slower than for viruses. The centrifugation is run just long enough for the smallest virus particles of interest to have enough time to band to the desired resolution in the gradient. This is typically within about 1–5% of the equilibrium position. The proteins will then primarily be to the low-density side of their equilibrium positions, as they started on that side. Since the equilibrium position of most proteins in a gradient is nominally about 1.3 g/ml, at the end of this shortened operating time, most proteins are positioned considerably lower than 1.3. The proteins are at positions which are not collected, and not sent on to the next stage as they are outside of the "virus window". Accordingly, the density-gradient centrifugation step takes on some of the properties of a combined two-stage density-gradient/sedimentation coefficient separation.

Once the viruses are banded, the centrifuge is decelerated to low speed, and the gradient is recovered by pumping the dense fluid of preferably 60% CsCl from the gradient supply system 15 to the outer edge of the annular space 13 through 14. The dense fluid displaces the gradient, with low density bands exiting first followed by high density bands. After gradient removal, the high density material in the rotor 12 is displaced by low density fluid, which enters from the inner rim of the annular space 13 at point 50 and displaces the high density material from the outer edge of the annular space 13. The procedure is complete in a few minutes, and the cycle repeats again beginning with the loading of the density gradient at low speed.

Ultracentrifugation provides the advantages of desorption of viruses from fomites and universal capture of all catalogued and non-cataloged viruses, with high capture efficiencies of greater than 95%. Ultracentrifugation also is not dependent on biochemical reagents, and provides a high degree of virus separation from the background components. Additionally, density information of the viruses is provided by the ultracentrifugation, providing the y-coordinate in the Virus Window plot, discussed herein. The coaxial seal 11 is commercially available as a Beckman's Zone Assembly, part no. 334241. Examples of the centrifuge rotor are the U.S. Army's B-VII, B-IX and B-XVI, or preferably the Beckman Spinco CF-32 Ti Continuous Flow Rotor, or Beckman's Z-60 rotor for ordinary zonal centrifugation. For the centrifuge itself; the Beckman Optima XL-100K Preparative Ultracentrifuge is well-suited for all of these rotors.

The results of the extraction of the ultracentrifugation of the centrifuge rotor 12 are analyzed from biological background by means of a "Virus Window." The Virus Window is a density-size (ρ-d) or density-sedimentation coefficient (ρ-S) plot of biological components which are pathogenic to humans, with the x-axis showing either size d or sedimentation coefficient S, and the y-axis showing density ρ, see FIG. 6. Mammalian viruses are approximately between 1.175 and 1.46 gm/ml density and have a diameter between about 22 and 200 nanometers (or, alternatively rephrasing this size range, with sedimentation coefficient between 120 and 6,000 Svedberg units). The Virus Window is an extremely useful concept not only because it shows how viruses can be separated from other non-viral background, but also because the different virus families are substantially separable from each other. Within the Virus Window, each virus family is distinguished by a particular rectangle with little overlap between the 20 family rectangles. Accordingly, with a known density and size, the detected virus particle is pinpointed to its particular family in the Virus Window. In any case, particles with densities and sizes that both fall in the Virus Window ranges can, with high confidence, be presumed to be viruses; thus when counts are registered in the detector of the present invention, having previously been selected by centrifugation for density in the range of about 1.175 to 1.46, and further selected by the Differential Mobility Analyzer for size between about 22 and 200 nm, then it can be concluded with a high degree of confidence that these indicate the presence of viruses in the sample. Furthermore, this confidence level is further increased if the density and size fall into a particular region of the Virus Window known to correspond to a virus. Similarly, other particles of potential interest in detection—such as prions, other virus-like particles, and other natural or artificial particles, colloids, cell structures, or macromolecules—will frequently have unique positions in the density-size plot that may allow them to be separated from other components and thereby be detected in the present invention.

Although to a very large degree only pathogenic viruses fall within the Virus Window, other background components fall close to the Virus Window. These components are microsomes and similar sub-cellular structures. These components can be effectively eliminated by adding nonionic surfactant, such as diethylene glycol monohexyl ether, to the collection stage 101 exit stream at inlet 4. The surfactant solubilizes the microsomes and membrane fragments. As recovery of viable viruses is not necessary, release agents can be used. The release agents are preferably organic solvents and surfactants, more preferably amphiphiles, and most preferably low molecular weight amphiphiles such as diethylene glycol monohexyl ether. The release agents provide several useful effects. First, they act to break up and even dissolve cellular substructures, such as microsomes, ribosomes, lysosomes, peroxisomes, and mitochondria, which have sizes and densities similar to viruses and set the limit on the required resolution, in the case of detection of viruses. Second, upon dissolution of the lipid envelope with such agents, the increase in the virus density is significant (the density of the viral core, which is the virus minus its lipid envelope, is in general significantly higher than that of the enveloped virus). In the case of hepadnaviridae, for example, this may be from about 1.25 to 1.36. Both effects serve to further differentiate viruses from, particularly, microsomes in the Virus Window plot, the first by acting to eliminate the microsomes, and the second by increasing the difference in density between the viruses and the background microsomes. Third, release agents enhance the desorption of viruses from solid matter, which is particularly important in the detection of airborne viruses. Release agents can also break up aggregates of viruses, especially aggregates of encapsulated viruses. The present invention minimizes this aggregation problem in other ways besides the use of release agents. The centrifugation can be performed without pelleting. Consequently, buoyant density, and thus isopycnic banding, is not greatly affected by aggregation under these circumstances. (Indeed, banding times are favorably reduced in the case of aggregation, and techniques can be applied that take advantage of this, within the broad context of the present invention). Any aggregation will generally produce only a small shift in, and/or broadening of, resulting virus bands. The portion of this exiting stream that contains the Virus Window is pumped to the purification stage 103 with the position of a particle along this stream giving the density of that particle. The useful part of the stream, in the case of general virus detection where the range 1.175–1.46 is passed to the next stage, is in the preferred embodiment on the order of about 10 ml; thus, this stage does not effect a large increase in virus concentration, though it does effect a very large increase in the concentration of viruses relative to other non-viral components.

Although feasible, a separate centrifugation to separate particles by sedimentation coefficient for Virus Window x-coordinate information is not necessary. A Differential Mobility Analyzer (DMA) 26, which as described below, provides rapid analysis of particle size. Additionally, separation of viruses from soluble proteins can also be done in the purification stage 103. An even further separation of proteins, and other macromolecules smaller than viruses, from viruses can also be done by tuning the supersaturation in a condensation particle counter so as to not detect macromolecules as small as proteins. The centrifuge dimension and rotor speed for optimal centrifugation can be calculated. Optimal times are preferably thirty minutes or less and resolutions are preferably 0.02 density units (0.02 gm/ml) or better.

The sample fluid passes from the extraction stage 102 into the purification stage 103. Typically, this could be in the form of 15 pulses, each on the order of 1–10 ml in volume, and each corresponding to a density slice with a width on the order of 0.02 gm/ml. In the purification stage 103, an ultrafiltration (UF) membrane 22 separates the viruses from soluble proteins (removing the need for a second, sedimentation rate centrifugation in the previous extraction stage 102), and concentrates particles with sizes greater than the pore size into a very small volume of liquid; additionally, in this stage soluble salts, including those from the sample as well as the density gradient material (e.g., cesium chloride), are greatly reduced in concentration. The UF membrane 22 may be Millipore's VIRESOLVE Membrane, an AMICON P membrane, or preferably a Pall FILTRON OMEGA Series membrane with a 1,000,000 molecular weight cutoff. The water permeability of the UF membrane 22 is on the order of 0.01 ml/cm$^2$-sec-psi, so that a membrane area of 0.1 cm$^2$ yields a flux of order 6 ml/min at 100 psig transmembrane pressure. The UF membrane 22 is incorporated into a housing which is designed to allow flow rates on the order of 0.1–20 m/min during ultrafiltration, which results in loading of the filter with particles larger than about 15 nm (which includes all virus particles), after which the particles are confined within a small front-face-side collection volume. A small-volume filtration filter holder 21, such as Schleicher & Schuell's SELECTRON, is used to hold the UF membrane 22. More preferably, a filter holder with a design like that of the SELECTRON, but made out of an alternative material which does not degrade electrolytically under high voltage, is used.

A four-way positioner 30 in the purification stage 103 allows automated processing of particles in the UF membrane 22. The positioner 30 is driven by a computer-controlled motor which positions the filter holder in one of four ports.

In the first position, the positioner 30 positions the UF membrane 22 to accept the sample flow outputted from the extraction stage 102. Each 0.02 gm/ml density slice from the output of the extraction stage 102 is, after passing through switch 10 in the second position, loaded through the UF membrane 22 in less than about 2 minutes; alternatively, larger density slices can be ultrafiltered, requiring appropriately longer times. A standard 0.2 micron poresize filter (such as available from Coming Costar) is preferably incorporated in the connection between the output from 102 and the input to 103, in order to remove any remaining particles greater than about 200 nm in size.

When the positioner 30 is switched to the second position, a valve closes off the sample flow and CsCl-free water from pump 18 out of tank 17 which has an inlet 16 is passed across the UF membrane 22 using on the order of 5 ml of water with a flux time of order 1 minute. This reduces the 30% CsCl aqueous solution surrounding the particles to less than 100 ppm CsCl, and allows recovery of the CsCl for recycling. Additionally, the amphiphile, viscosity additives and buffer components are reduced in the UF membrane 22. More preferably, ammonium acetate solution, with on the order of 20 mM concentration in water, is used for this operation, preparing the liquid for downstream detector stage operation.

On switching the positioner 30 to the third position 19, the pure water (or ammonium acetate solution) is shut off, and a final ultrafiltration is performed in order to reduce the volume of liquid on the retentate side of the membrane, thereby greatly increasing the concentration of viruses and reducing the volume of liquid to the small quantities required for operation of the detection stage 104; the filtrate in this step passes out through port 23. More precisely, the UF stage 103 is integrated with the electrospray assembly 24 of the detection stage 104 by a punctured disk fitting. The fitting has a 150 micron hole drilled through a tubular stub in its center. When positioner 30 is in the third position, this hole allows the filtrate to pass out through port 23. When the positioner 30 is in the fourth position, the inlet end of the electrospray capillary 29 (the end opposite the spray tip) is inserted into this 150 micron hole. This fits in a piston-like manner into the stainless steel cylinder of the SELECTRON (or SELECTRON-like) filter holder. The cylinder slides over the steel disk, and is positioned with a gap between the steel disk and the ultrafilter surface on the order of 100 microns.

In the fourth position 20, in accordance with the above, the UF membrane 22 is positioned for entry of the virus containing retentate into an electrospray capillary 29 of the detection stage 104. (Alternatively, instead of fluid passing directly from the purification stage 103 to the electrospray, an intermediate component may be used to accomplish a further purification and/or concentration). A platinum wire may be run from the voltage source of the electrospray unit 24 to the interior of the liquid inside the volume on the retentate side of the UF membrane, in order to establish a current return for the electrospray operation.

The detection stage 104 accomplishes several functions, which include a final purification, an individual virus particle count and a size determination of the detected particles. The detection stage 104 includes three major components, an electrospray assembly (ES) 24, a Differential Mobility Analyzer (DMA) 26 and a Condensation Nucleus Counter (CNC) 27, which is alternatively called a Condensation Particle Counter (CPC). The components may be commercially obtained individually from TSI, Inc. of St. Paul, Minn. The Condensation Nucleus Counter 27 and Differential Mobility Analyzer 26 units are also available commercially from TSI as a single integrated unit, which can be accompanied by an IBM PC with associated software. This allows for an inexpensive set up compared to a mass spectrometer. The detection stage 104 can conduct measurements concurrently with the collector 1 obtaining the next cycle's collection.

Passing from the purification stage 103, the retentate enters the detection stage 104 at the inlet of the electrospray capillary 29 of the electrospray assembly 24 in the fourth position of the positioner 30. Entry into the electrospray capillary 29 is done without passing the retentate through piping, which might cause sample losses. The electrospray capillary 29 is on the order of 25 cm in length, and the inlet of the electrospray capillary 29 is positioned to the small front-face-side collection volume of the UF membrane 22, as described above. The electrospray capillary 29 is then positioned to sample liquid from the retentate-side of the filter and the sample liquid enters the electrospray assembly 24.

In the electrospray assembly 24, the liquid sample solution is passed into an orifice or "jet" of 50 micron diameter, and droplets are ejected under the influence of an electric field. The droplets are typically between 0.1 and 0.3 microns in size, with a fairly narrow size distribution. At a droplet size of 0.3 micron, sampling rates are 50 nl/min (50 nanoliters/minute), allowing the electrospray assembly 24 to spray the collection volume in on the order of 20 minutes per microliter.

From the electrospray assembly 24, the sample passes to a charge neutralizer 25. The charge on the droplets is then rapidly recovered using an ionizing atmosphere to prevent Rayleigh disintegration. The neutralized ES droplets are then dried in flight, leaving the target virus molecules and/or dried residue of soluble impurities. From the charge neutralizer 25, the target virus molecules and/or dried residue enters the Differential Mobility Analyzer 26.

The Differential Mobility Analyzer 26 uses electrophoretic mobility of aerosol particles to classify the particles by size, using the inverse relationship between the mobility of a particle to its size. In the Differential Mobility Analyzer 26, particles are carried by an air stream at a set velocity through an electric field created by a charged rod. If the particle is singly and positively charged, it experiences an electrostatic attraction to the rod, which competes with the inertial force of the flow. When the electrophoretic mobility falls in a certain range, the particles pass through a narrow exit port at the end of the charged rod. The particle size range, which is generally 0.01 to 1 micron, is divided into 147 size channels. The entire range is automatically scanned in 1 to 10 minutes, generally 3 minutes. The Differential Mobility Analyzer 26 has only a possible 3% instrumental error for virus size determination. Additionally, there is a possible size increase due to the covering of the virus particle with impurity residue, which at an impurity level of 100 ppm, a typical 40 nm virus has a possible error of up to about 2% in effective size. If the impurity levels are less than 20 ppm, the error becomes smaller than 1%.

When the primary droplets from the electrospray assembly 24 are 0.3 micron, a 1 ppm soluble impurity creates a 3 nm residue particle, and a 125 ppm soluble impurity creates a 15 nm particle. Particles which are 15 nm in diameter can be separated in the Differential Mobility Analyzer 26 from viruses which are at least 22 nm in diameter. Accordingly, soluble impurities must be reduced to less than 100 ppm (0.01%) to avoid background interference with virus signals.

Detection of proteins at levels of $10^{11}$–$10^{12}$ molecules/ml indicates that a sensitivity level for viruses of $10^{10}$ particles/ml can be achieved, and possibly $10^9$ particles/ml, particularly by combining the Differential Mobility Analyzer 26 selection with an adjustment of the Kelvin radius of approximately 10 nm. Impurities of 1 ppm yields a 3 nm residue particle which can overlap protein sizes. Impurity levels of 100 ppm or less are acceptable in the detection of viruses, since viruses are several times larger than proteins. Sensitivities of $10^{10}$ molecules/ml and possibly $10^9$ molecules/ml are projected based on documented results using proteins. In one of the Examples given below, detection of $10^{12}$ pfu/ml (a pfu is a plaque-forming unit) was easily accomplished even after dilution by a factor of 128, demonstrating detection at a level of $10^{10}$ pfu/ml.

The Differential Mobility Analyzer 26 validates against false positives by changing the dilution and seeing whether the particle size also changes. Additionally, the Differential Mobility Analyzer 26 can be used to provide another layer of protection against interference from impurities up to the 100 ppm level. The level of $10^{10}$ molecules/ml corresponds to $2\times10^7$ viruses in a 2 microliter collection volume of the purification stage 103, and $10^9$ molecules/ml corresponds to $2\times10^6$ viruses. At a collection volume of $10^7$ viruses of the present invention, or 20 minutes of XM2 sampling, 20,000 liters (20 $m^3$) of air are sampled. Accordingly, the sensitivity of the present invention is on the order of 500 viruses per liter of air. With impurity levels of 100 ppm or less, virus size can be determined by the Differential Mobility Analyzer 26 to within about 4%. The detection stage requires on the order of 5 to 40 minutes, including Differential Mobility Analyzer 26 size determination, and can be preformed concurrently with centrifugation for a subsequent cycle.

From the Differential Mobility Analyzer 26, the sample enters the Condensation Nucleus Counter 27, which uses a nucleation effect. The aerosol sample enters and passes through a heated conduit having an atmosphere which is saturated in butanol. The sample is routed into a cooled condenser, where butanol vapor condenses onto the sample particles, which act as nuclei. The saturation is regulated so that no condensation occurs on the nuclei below a critical size, which limits false background counts to less than 0.01 particle/ml. With nucleating particles, condensed droplets grow to micron size and are optically detected using a 780 nm laser diode with photodetector. Provided that the level of impurities is low enough that the residue particles are below the threshold of detection by the Condensation Nucleus Counter 27, and/or are separated from the target molecules by size, then only the target molecules will be registered with the Condensation Nucleus Counter 27. As the nucleation of droplets does not depend on surface characteristics of the particles, butanol saturation can be adjusted for a critical size of 0.01 micron radius which minimizes background counts from proteins and other soluble impurities. Response times for step changes in concentration are less than 20 seconds, and operation of all components is in the temperature range from 10° C. to 38° C. Supersaturation tuning for a 10 nm Kelvin radius threshold in the Condensation Nucleus Counter 27 can be used to cancel the detection of non-viral impurities, including proteins, provided they are below about 100 ppm.

The ultrafiltration stage has an output volumetric rate which is very well suited for input into the ES-DMA-CNC particle counter, which addresses the strict requirements and narrow range of operating parameters for the ES-DMA-CNC unit. In recognizing the high value of this molecule-counting and molecule-sizing ES-DMA-CNC unit, ultrafiltration provides excellent samples for the purification/concentration stage prior to this detector. The ES-DMA-CNC combination allows particles to be sized and permits improved sensitivity by an order of magnitude over a DMA-CNC combination. Protein concentrations of 10 mg/ml, or $10^{11}$–$10^{12}$ molecules/ml, can be detected and sized.

The system is controlled by a computer 28. When data collection and instrument control are handled by the same computer, the computer may vary the mode of operation in response to virus detection. Initially, before viruses have been detected, the system places the entire 300 ml of density gradient from the extraction stage 102 through the UF membrane 22 to scan all virus sizes from 22 to 200 nm. Alternatively, the Differential Mobility Analyzer 26 is by-passed entirely, provided that non-viral concentrations are low enough that tuning of the Kelvin radius in the Condensation Nucleus Counter 27 is sufficient to reduce background. Once viruses are detected, the Differential Mobility Analyzer 26 indicates the sizes of the viruses detected. The computer can then trigger the output of the extraction stage 102 to be sampled piecewise in the purification stage 103. By breaking the range of virus densities, which is about 0.3 gm/ml into 10 or 15 slices, the density of the detected virus is within about 0.02–0.03 gm/ml, which is sufficient to narrow most viruses down to a single family. Following this, the region in the centrifuge output stream surrounding this density can be divided still finer, to provide better accuracy on the viral density. Through data base comparison, the system identifies the viral families from the measured densities and sizes, and provides output of detected viruses by density, size, concentration, apparent changes in concentration over time, and if desired, audible and/or visual alarms in the presence of detected viruses. Being automated, the instant invention can run continuously for long periods of time without an operator. In addition to making continuous virus monitoring possible at a large number of sites simultaneously without the need for scores of virologists, the automation afforded by the present invention also limits the risks of viral infection of technicians.

Other physical means of separating viruses and other particles from background and/or enriching their concentration, which are substantially equivalent in their effect to the purification and concentration means discussed above, and which can be applied in addition to or in substitution for these means without departing from the spirit or scope of the present invention, include capillary electrophoresis (purification and concentration enrichment), sedimentation-rate centrifugation (primarily purification), hydroextraction (mainly concentration), dialysis (purification and concentration), organic/inorganic flocculation (purification and concentration), and capillary chromatography, which can size-exclusion, hydrophobic interaction, or ion-exchange chromatography (purification and concentration).

EXAMPLES

Analysis of two blind samples was performed, using the ultrafiltration (UF) stage and the electrospray (ES)—differential mobility analyzer (DMA)—condensation particle counter (CPC) triage, or gas-phase electrophoretic mobility molecular analyzer (GEMMA).

Filtration: Two samples, labeled as AFO001 and AFO682 were obtained. AFO682 had been collected and contained viruses; AFO001 was a blank or control, although the foregoing was not known about the two samples prior to testing. Each original sample was on the order of 1.2 ml in volume. From each sample, all but about 200 microliters was taken and prefiltered, through a 0.2 micron poresize Millipore syringe filter with low dead volume. Approximately 400 microliters of this was removed in each case and processed in an ultrafiltration unit designed and built for this purpose. A 500,000 MW cutoff membrane was selected to separate viruses, which were retained, and to pass proteins and soluble salts out in the filtrate, which were discarded. Successive diafiltration was used, with each filtration step concentrating retained material into a volume of about 5 microliters on the retentate side of the membrane. Between successive filtrations, 20 mM ammonium acetate solution was used to restore the volume to about 400 microliters. This strength of ammonium acetate was used for the proper operation of the electrospray (ES), in the detection stage. After two successive diafiltration steps, two 100 microliter portions of the final, ultrafiltered sample were collected in two ways. The first 100 microliters was obtained by forcing out 100 microliters of the retentate volume back through a port which was forward or upstream of the membrane surface, during the final leg of the last diafiltration. This was done after allowing 20 minutes for diffusion of the viruses away from the membrane surface. The second 100 microliters was obtained by using a gas-tight syringe press-fit into the filtrate outlet port, to push ammonium acetate buffer backward across the membrane, from the filtrate side to the retentate side, in order to elute virus from the membrane. The design of the ultrafiltration unit was such that the retentate side of the membrane remained in a water environment, avoiding for example, an air-purge or vacuum flush of the system causing irreversible adsorption and breaking of virions.

Detection: The filtration resulted in three 200 microliter samples for each of the two specimens: one before filtering, one prefiltered, and one prefiltered and ultrafiltered. The samples were placed in Eppendorf vials. Each sample contained ammonium acetate, which is important in maintaining the conductivity necessary for electrospray operation. Being volatile, it decomposes and evaporates into ammonia and acetic acid during the in-flight drying of the electrospray-generated aerosol, and so does not contribute to the final scan. Additionally, each sample contained the viral particles and fragments of interest. Furthermore, each sample contained soluble salts, which are not volatile and thus lead to a "residue particle" after in-flight drying. For example, with the electrospray set at 300 nm droplets, a salt level of 1 ppm would yield an average residue droplet diameter of $(1/10^6)^{1/3}$×300 nm=3 nm. Very high salt concentrations can increase conductivity and destabilize the electrospray, which in all the data shown, was not a problem. However, in some scans shown for samples that were not ultrafiltered, the salt peak from these residue particles extends out to as high as 15 nm.

Samples were input by inserting a capillary into the Eppendorf vial. Flushes of pure, 20 mM ammonium acetate were run before and between samples. Stability of the electrospray is in general indicated by a current between 200 and 400 nA.

Figure 2A:
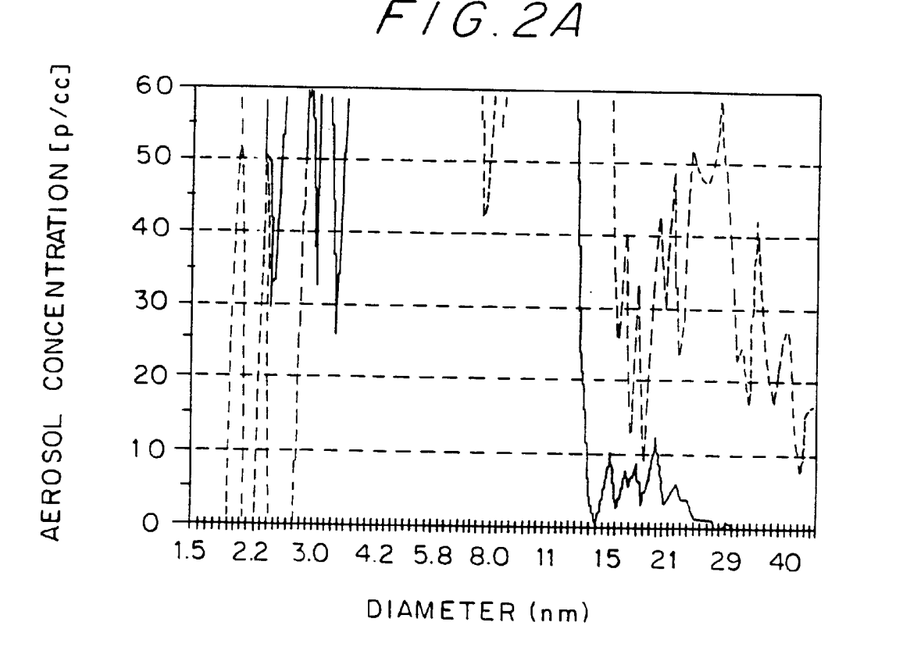
FIGS. 2A and 2B each compare DMA-CNC data for a typical sample before and after ultrafiltration, where the solid curve shows data before ultrafiltration and the dashed curve shows data after ultrafiltration.
Figure 2B:
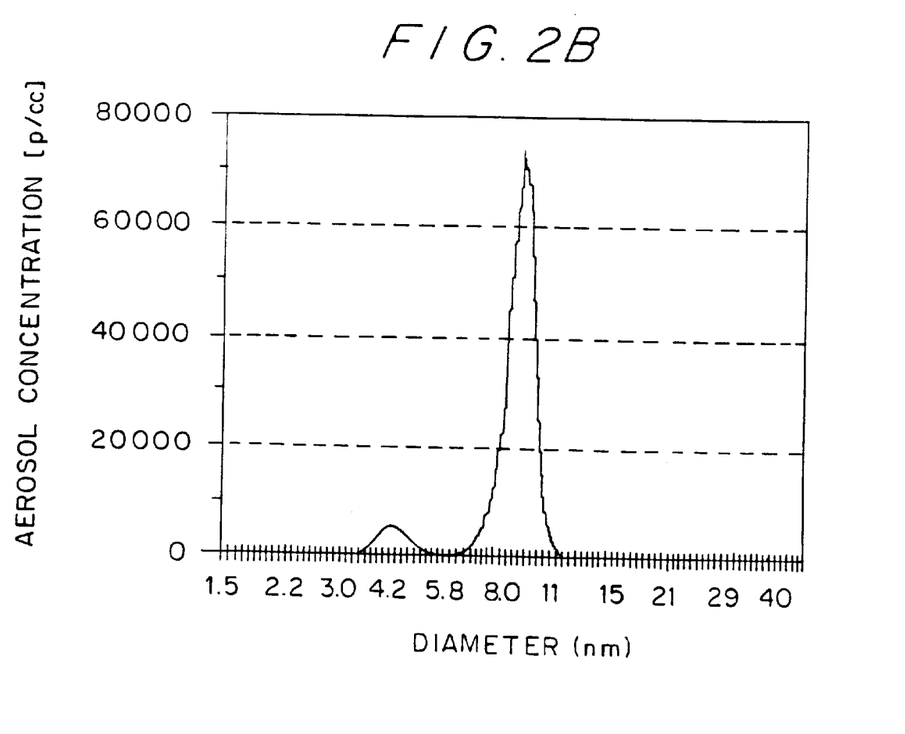

Results: FIGS. 2A and 2B each compare DMA-CNC data for a typical sample before and after ultrafiltration, both being pre-filtered. In each of these two figures, the solid curve shows data before ultraflitering and the dashed curve after ultrafiltering. In FIG. 2B the peaks centered at about 9.0 nanometers and at about 4.2 nanometers represent background peaks due to soluble impurities (mainly salts) before and after ultrafiltration, respectively.

FIG. 2A, which focuses on the 15–40 nm range where the number of counts is low, show a solid curve for the 'before ultrafiltered', which was diluted by a factor of 16 before running, with a dashed curve for the ultrafiltered sample run at full strength. This plot, which was reproduced over a number of scans, shows the two curves tracking each other well into the region above 15 nm, with the ratio starting well above 1:16 (roughly 1:4) but approaching this at larger diameters. This shows that the ultrafiltration retained this material well, at least as the diameter increased to above 20 nm, but even fairly well between 15 and 20 nm; the MW cut-off curve of the UF membrane rises from 0 to 90+% retention between about 10 and 20 nm., significant since intact virus particles, those lying in families known to be infectious to mammals, are always greater than 20 nm.

In FIG. 2B, the dashed curve shows data after ultrafiltration in comparison with the solid curve before ultrafiltration. FIG. 2B shows a greatly reduced salt content, given by the cube of the diameter ratio, and remarkable reductions in protein concentrations. The protein concentration are in the range of 7–15 nm, in which many proteins lie, particularly, proteins higher than about 80,000 MW. The data under the solid curve are for the non-ultrafiltered sample at 1/16th strength, so that the reduction is even more dramatic than as appears in the plot. As plot 2A, above, showed that the 15+ nm fraction was preserved by the ultrafiltration, even quantitatively above 20 nm. The reduction in the salt peak was also extremely good, both in intensity and in the lowered diameter, pushing it down away from the region of interest. This indicates that the ultrafiltration methodology is extremely effective for removing soluble salts and proteins, while preserving 20 nm and greater fractions. It is evident that the ultrafiltration reduced the background, which is due to the salt residue particles, both in magnitude and location, shifting the peak position for the background from about 11 nm to about 5 nm, putting it well below the range of interest for virus detection.

The experimental results of an environmental source sample was analyzed with the UF-ES-DMA-CNC combination. As a blinded experiment, the components of the two samples were not known, except that one sample could be a "blank", with no viruses, and the other sample was either doped with virus or was an environmental sample, collected from sampling of air in the wild. Upon analysis of the DMA-CNC data, viruses were detected and counted in one sample, AFO682, and no viruses detected in the second sample.

Figure 3:
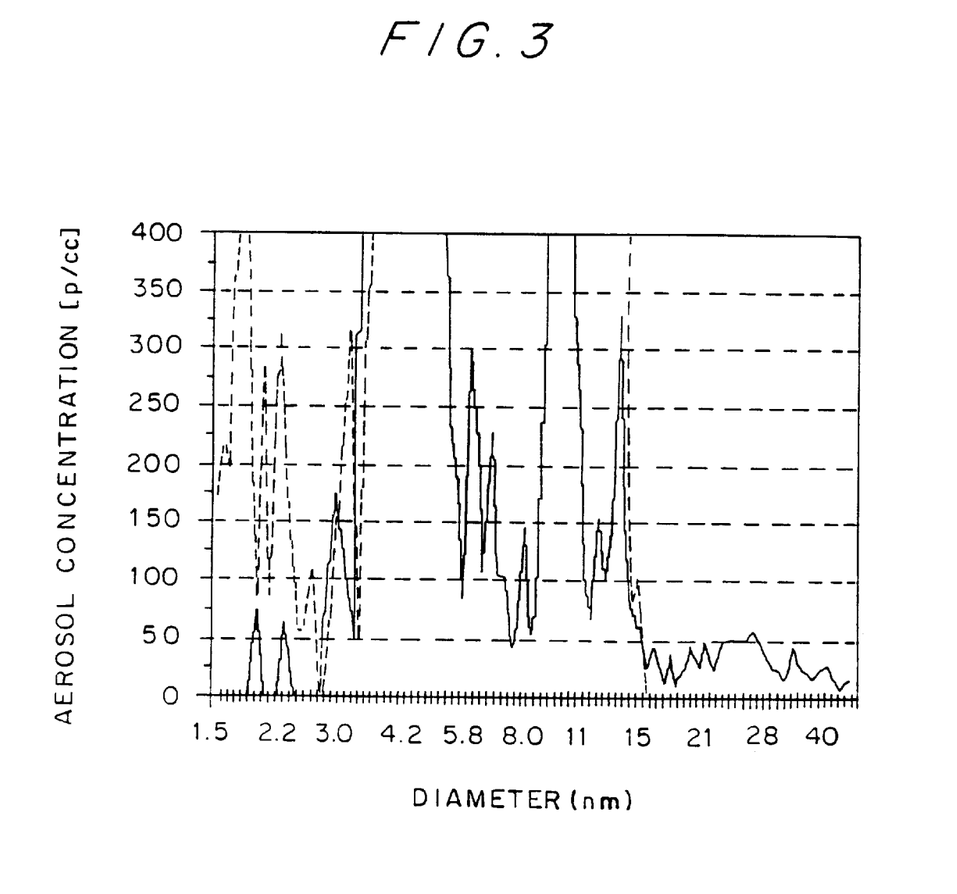
FIG. 3 shows a plot of the GEMMA data for two ultrafiltered samples;.
Figure 4:
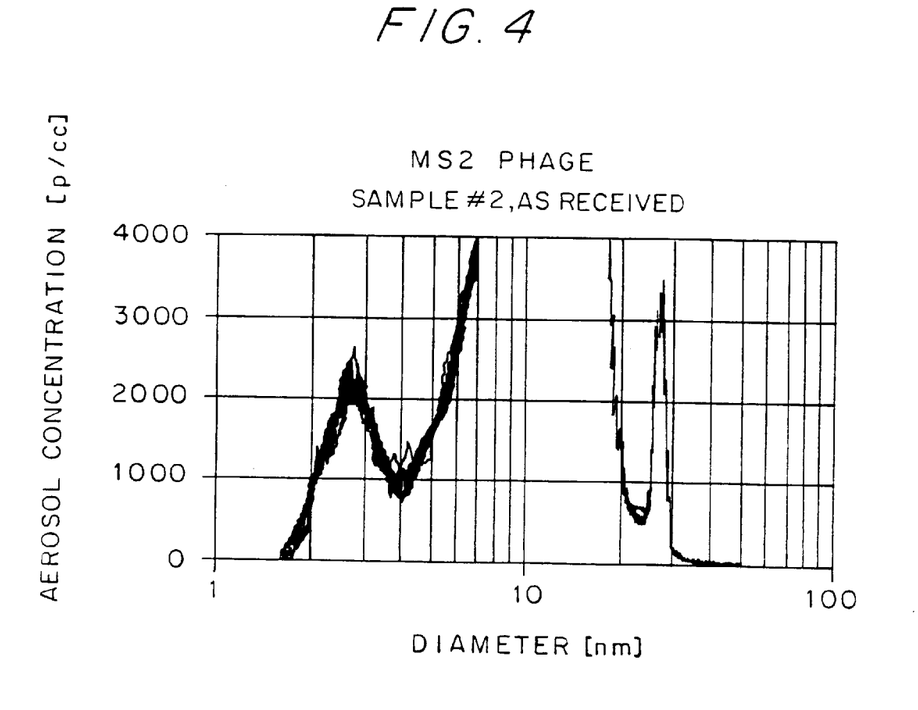
FIG. 4 shows a plot of GEMMA data for MS2 phage for four runs of a known standard sample after ultrafiltration.
Figure 5:
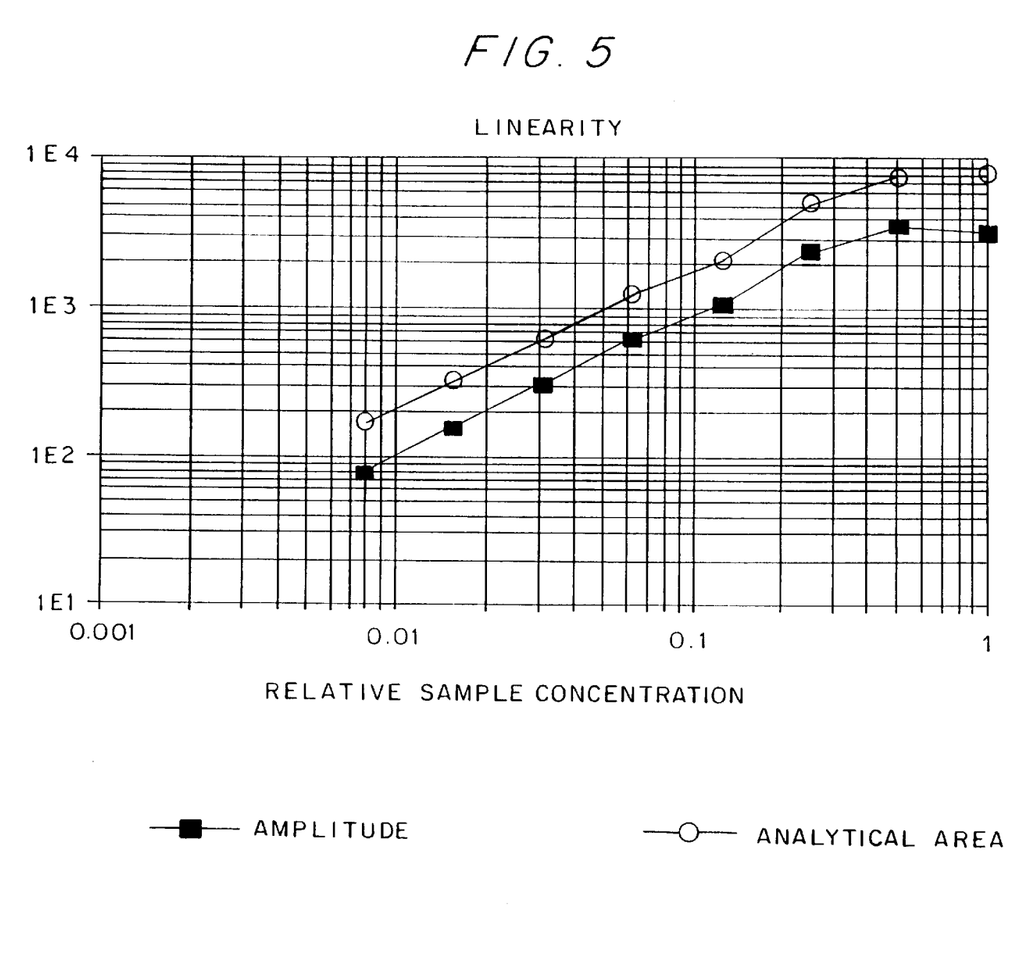
FIG. 5 shows peak amplitudes and areas plotted as a function of successive dilutions of the sample of FIG. 4.

FIG. 3 shows a plot of the GEMMA data for the two ultrafiltered samples. The x-axis gives the particle size in nanometers, and the Y-axis gives a concentration measurement. Evidence of particles in the range of 22–40 nm was shown, the range for intact virus particles, in sample AFO682. In sample 682, the counts here are quite low, and translated into concentrations on the order of $10^{10}$ particles/ml or 10 femtomoles per ml, after filtering. In sample AFO001, there is essentially no activity measured in the range 22–40 nm, where background counts are typically 0, or at most 8 counts. With isopycnic banding information from the centrifuge stage, a double-check to distinguish between simple protein aggregates or polysaccharides with gravimetric densities of about 1.3 or less, and unenveloped viruses of about 1.4 is possible. Upon use of the full system including centrifuge, the locations of the viral families in density-size space could be mapped systematically, providing a look-up table that would be useful for distinguishing between viral and non-viral material.

FIG. 4 shows data for a similar analysis on a known sample, prepared of MS2 bacteriophage of known concentration, $10^{12}$ pfu/ml. After ultrafiltering 0.5 ml of the known sample as described above for the blind samples, without prefiltering, a 50 microliter sample was analyzed with the ES-DMA-CNC combination. FIG. 4 shows that the virus was easily detected, and the virions are counted and sized. The size obtained from the DMA was 26 nm, in agreement with literature for scanning electron microscopy (SEM) analysis on Leviviridae. The linewidth (full-width at half-max, or FWHM) was small at only 2 nm, indicating that the size can be determined very accurately and that viruses of a single type can be distinguished from other viruses and non-viral particles with high reliability.

In addition, the ultrafiltered known sample in FIG. 4 was diluted successively by factors of 2, down to a dilution of 128, and analyzed in the ES-DMA-CNC. Even at 1/128, the peak was still easily distinguished, giving a signal-to-noise ratio of approximately 10:1. FIG. 5, shows the peak amplitudes and areas which are plotted as a function of dilution (relative sample concentration, with the undiluted sample having a value of unity). FIG. 5 demonstrates the linearity of the detection method.

It should be understood that the foregoing summary, detailed description, and drawings of the invention are not intended to be limiting, but are only exemplary of the inventive features which are defined in the claims.

What is claimed is:

1. A system for the detection of the presence of submicron sized particles, comprising:

(a) means for extracting submicron particles from a sample based on density;

(b) means for purifying said extracted submicron particles by concentrating said particles based on size; and (c) means for detecting said extracted and purified particles, wherein said detecting means comprises: an electrospray assembly, said assembly having an electrospray capillary which receives output from said purifying means; and a differential mobility analyzer which receives the output from said capillary.

2. The system of claim 1, further including a charge neutralizer which receives the output from said electrospray assembly prior to said differential mobility analyzer.

3. The system of claim 1, wherein said electrospray capillary is directly integrated with said purifying means.

4. The system of claim 1, wherein said differential mobility analyzers scans for particles having sizes from about 0.01 to about 1.0 micron.

* * * * *